United States Patent [19]

Milne

[11] Patent Number: 5,302,122
[45] Date of Patent: Apr. 12, 1994

[54] DENTISTRY IMPLANT PARALLELING DEVICE AND METHOD OF INSTALLING IMPLANTS

[76] Inventor: Robert H. Milne, 700 NE. Multnomah, Portland, Oreg. 97232

[21] Appl. No.: 42,712

[22] Filed: Apr. 5, 1993

[51] Int. Cl.$^5$ .................................................. A61C 3/02
[52] U.S. Cl. ........................................ 433/76; 433/173
[58] Field of Search ................................. 433/76, 173

[56] References Cited

U.S. PATENT DOCUMENTS

| | | | |
|---|---|---|---|
| 1,321,130 | 11/1919 | Schlueter | 433/76 |
| 2,303,475 | 12/1942 | Karlstrom | 433/76 |
| 3,078,580 | 2/1963 | Galvez | 433/76 |
| 3,254,413 | 6/1966 | Suga | 433/76 |
| 4,344,755 | 8/1982 | Gold | 433/76 |
| 4,964,801 | 10/1990 | Kawahara et al. | 433/173 |
| 4,998,881 | 3/1991 | Lauks | 433/76 |
| 5,015,183 | 5/1991 | Fenick | 433/76 |

*Primary Examiner*—John J. Wilson
*Attorney, Agent, or Firm*—Eugene M. Eckelman

[57] ABSTRACT

An articulated arm has a post on one end that guides a handpiece at a selected angle. The other end of the arm has a bore capable of supporting the arm at this other end in cantilevered arrangement on a base fitted in a hole drilled in the jaw that has been made to receive an implant or a base on a non-implant appliance. The articulated arm has at least two pivotally connected identical links that maintain the handpiece in parallel relation with the base whereby in the method of the invention implants can be installed that are parallel with each other or with a non-implant base.

10 Claims, 2 Drawing Sheets

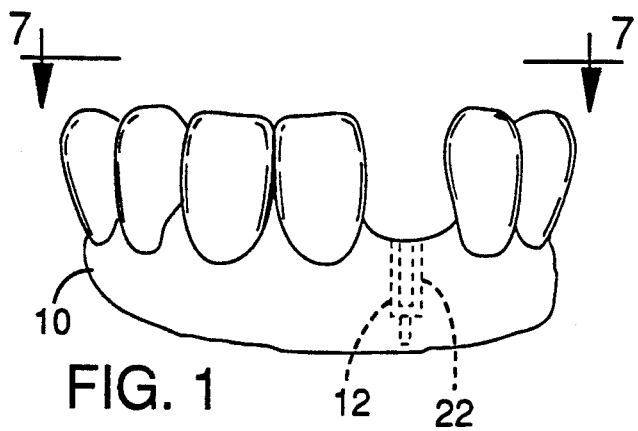
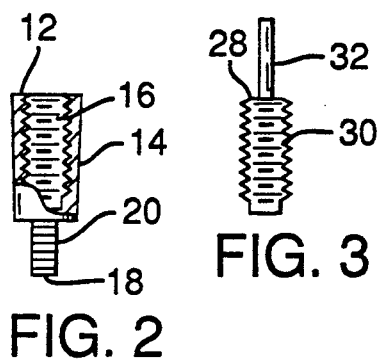
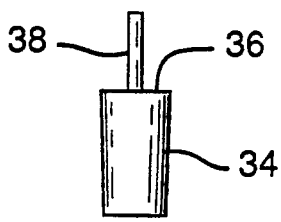
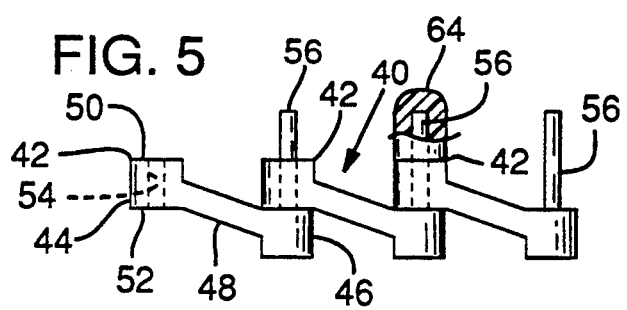
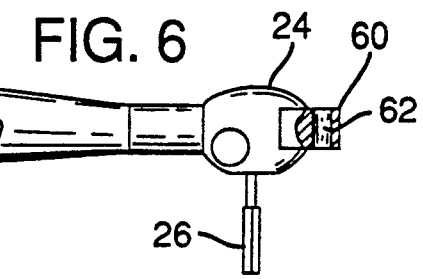
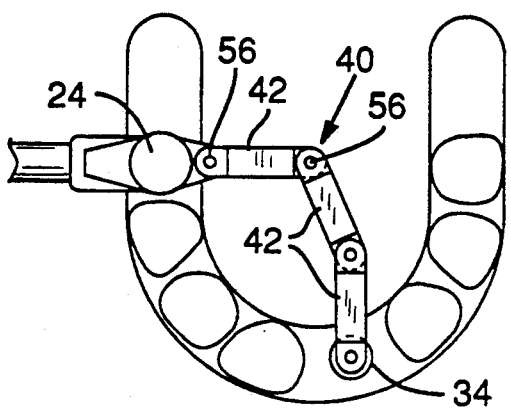
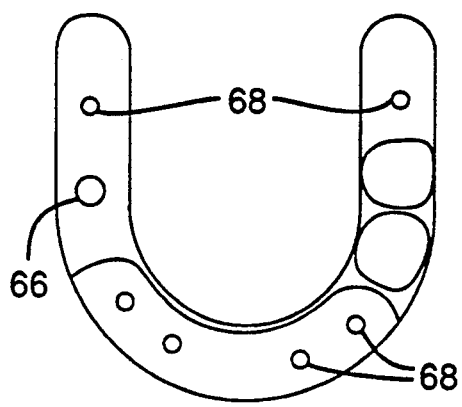

DENTISTRY IMPLANT PARALLELING DEVICE AND METHOD OF INSTALLING IMPLANTS

BACKGROUND OF THE INVENTION

The present invention relates to a dental device that functions to assist in placing implants parallel with each other or parallel with a non-implant appliance supported in the mouth, and to a method of installing implants in parallelism. This allows precise placement of implants at angles and sites as determined by presurgical models, radiographs and stints.

Implants are now commonly used for providing anchor points in the jaw to which supports are made for a single tooth, for multiple teeth, and/or for bridges, etc. If more than one implant is to be inserted in the jaw or if implants are to be used in combination with existing non-implant appliances, it is highly desirable that all the implants be parallel with each other. This parallelism makes for precise and uniform angulation of implants in the jaw for best results. Such parallelism also makes for precise abutments in anchor teeth for bridges and the like since such abutments allow convenient and accurate on and off fitting of bridge supports.

Devices have heretofore been employed for drilling parallel abutment surfaces in teeth for installation of bridges, crowns, etc. An example of such devices is shown in U.S. Pat. No. 4,344,755. In this patented device, a base portion is used that is secured temporarily to existing teeth by dental silicone or other impression type material. A parallel link assembly is pivotally and rotatably combined with the base portion and supports a dental handpiece or drill in an arrangement such that the cutting axis of the burr of the handpiece is parallel with an established axis on the base portion and can be rotated to prepare the abutment. This prior device and others were not designed for use in connection with establishing parallelism between two or more implants or between a mechanical post supported in the mouth and other implants, and thus cannot function as such.

SUMMARY OF THE INVENTION

According to an object of the invention, a dentistry implant device and method are provided that function to establish parallelism between implants. Such device and method are simplified both in their use and construction.

The device has a laterally articulated arm with guide means at the free end thereof capable of guiding a handpiece at a selected angle. The other end of the arm has support means capable of supporting the arm in cantilevered arrangement on a projecting base that is associated with a person's mouth and that provides parallelism for the handpiece guide. Such base may be a hole drilled in the jaw that has been made to receive an implant or to act as a pilot hole, or it may be associated with a non-implant member in the mouth such as a splint or other appliance. The handpiece may have a permanently attached guide portion thereon for functioning with the guide means at the free end of the articulated arm, or in modifications of the invention a removable adapter link can be provided that receives the shank of a burr, or also the burr itself can be guided in an end link of the articulated arm. The laterally articulated arm is constructed of at least two pivotally connected links that have means to maintain the arm in a rigid cantilevered arrangement whereby the handpiece is guided in parallel relation with the base. The method of the invention provides parallel mounting of implants in a jaw as related to an initial implant or non-implant appliance associated with the mouth.

The invention will be better understood and additional objects and advantages will become apparent from the following description taken in connection with the accompanying drawings.

BRIEF DESCRIPTION OF THE DRAWINGS

FIG. 1 is a fragmentary front elevational view of a portion of a person's jaw showing an implant installed therein of the type with which the present invention is concerned.

FIG. 2 is a side elevational view, partly broken away, of the implant prior to installation.

FIG. 3 is an elevational view of an insert portion of the implant of FIG. 2, this insert portion being arranged to form an anchor point for tooth members or other devices such as bridges.

FIG. 4 is an elevational view of a temporary anchor member forming a part of the invention.

FIG. 5 is a side elevational view of the articulated arm of the invention capable of cantilevered support on the temporary anchor member of FIG. 4 when the device of the invention is used.

FIG. 5A is an isometric view of on of the links of the articulated arm of FIG. 5.

FIG. 6 is a fragmentary side elevational view of a dental handpiece showing alteration thereof for purposes of the present invention.

FIG. 7 is a fragmentary plan view of a person's jaw and showing use of the present device in installing implants, and FIG. 8 is also a fragmentary plan view of a person's jaw but showing an example of tooth and bridge support locations of implants that are readily aligned by the present invention.

DETAILED DESCRIPTION OF A PREFERRED EMBODIMENT

Figure 9:
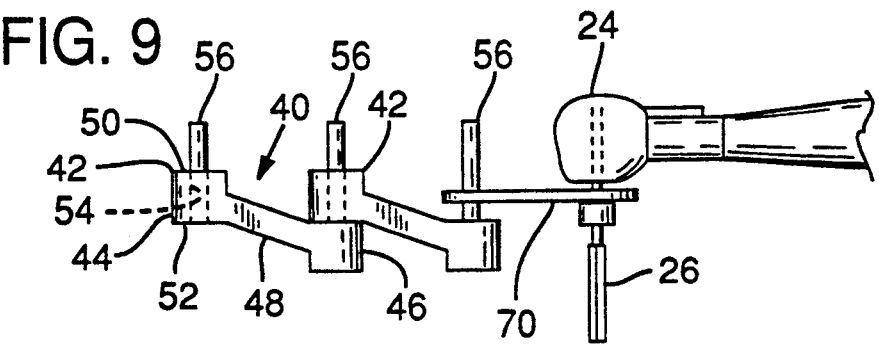
FIG. 9 is a side elevational view of a modified form of connecting means between the articulated arm and the handpiece.

With particular reference to FIG. 1, a portion of a person's jaw 10 is illustrated and includes an implant 12 installed in an area of the jaw that is absent one or more teeth. The implant 12 is detailed in FIG. 2 and comprises a cylindrical body member 14 having an internally threaded bore 16 and a depending stem 18 provided with transverse openings 20 for receiving healing bone growth after installation of the implant. The implant has a slight overall taper inwardly toward the stem end and is fitted in a correspondingly shaped hole 22 made in the jaw bone by the dentist handpiece 24 and detachable burrs 26, FIG. 6. The hole 22 is made by starting with a small burr and enlarging the hole 22 by successively larger burrs to the outer diameter and shape of the implant 12. After the implant is installed and healed in place, it receives an insert 28 having an exterior threaded surface 30 that threadedly engages bore 16. Insert 28 has a post 32 at one end that is engaged by the tooth or bridge to be anchored. The structure thus far described is conventional.

Often, it is desired to install multiple implants in a jaw bone, and it is particularly desirable that the implants be parallel with each other. It has been found that it is substantially impossible to provide such parallelism merely by sight and guesswork when drilling the implant holes 22. According to the invention, a temporary anchor member or base 34, FIG. 4, is used that has an exterior shape and diameter throughout its length corresponding identically to the exterior shape and diameter of the implant body portion 14. Thus, this anchor member, being of the same shape and size as the implant body portion 14 can be fitted in the implant hole 22 prior to installation of the implant 12. Since the tolerances between the hole and the members 14 and 34 are fairly close, the anchor member 34 will have a substantially firm mounting in the implant hole to serve as a temporary support and pivot guide, to be described. The temporary anchor member 34 has a flat top surface 36 extending at right angles to the axis of the member 34. A post 38 extends upwardly in integral axial relation from the member 34.

Also forming a part of the present invention is an articulated arm 40, FIG. 5, made up of a plurality of identically shaped links 42. Each of the links comprises opposite heads 44 and 46 and an integral angled body portion 48 between these two heads. Each of the heads 44 and 46 has opposed surfaces 50 and 52. Heads 44 have an axial bore 54 that opens through surfaces 50 and 52. The surface 52 extends at right angles to the bore. Each head 46 has an integral upright post 56 extending at right angles to the surface 50 and thus parallel with bore 54. The offset relation of the heads 44 and 46 due to the angled body portion 48 is such that in the stacked relation of the links 42 as shown in FIG. 5, wherein the posts 56 engage in a bore 54 and the surfaces 52 of the second and succeeding links 40 are in engagement with the surfaces 50, the surfaces 52 of the heads 44 are all aligned in the same longitudinal plane. Thus, the links are supported in a straight cantilevered plane relative to each other but have independent pivoting lateral movement. They cannot twist sideways, however, and thus all posts 56 will be maintained in parallelism with an end bore 54.

For use with the invention, the handpiece 24 in one embodiment is provided with an attached front guide 60, FIG. 6, with an upright bore 62 therein arranged to snugly but slidably and pivotally receive a post 56 of links 42.

In the use of the present implant paralleling device, and assuming that multiple implants are being made and for best results need to be parallel with each other, the temporary anchor member 34 is placed in the implant hole 2 after the latter has been precisely drilled but prior to receiving the implant 12. With the anchor member 34 snugly fitted temporarily in place, the articulated arm 40 is mounted on the post 38 of this anchor member by engaging the axial bore 54 of an end head 44 with the post 38. Since the links 42 will stack in a precise flat untwisting relation, the post 56 of the end link will be parallel with the post 38 of the temporary anchor member 34. The guide portion 62 of the handpiece is thereupon engaged with the post 56 of the end link 42 and implant holes made by the burr 26 and succeeding burrs will be parallel with the first implant 12. Thereupon, any number of implants can be made in the jaw bone by using a suitable number of the links and shaping the arm as necessary to reach the desired point to avoid other teeth or bridges if necessary.

Removable friction caps 64 are preferably used on projecting portions of posts 56, as illustrated with one of the posts in FIG. 5, to prevent separation of the links 40 while the device is in operation. Such caps will also allow the arm to be inverted when used on the upper jaw.

FIG. 7 is an example of paralleling method of the present device. In this example, an implant is to be placed in a molar area of the jaw bone in addition to the implant 12 at the front shown in FIG. 1. Prior to permanently installing the first implant, namely, the implant 12, the temporary anchor member 34 is mounted in hole 12 made for this implant and the present arm 40 used to position the handpiece 24 in such molar location for drilling a hole precisely parallel with the hole in which the temporary anchor member 34 has been placed. With reference to FIG. 8, multiple implant holes in parallel relation with a first implant hole 66 can be made at selected points 68 arranged for single tooth or bridge support.

Figure 10:
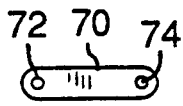
FIG. 10 is a top plan view of a connector plate used with the FIG. 9 embodiment.
Figure 11:
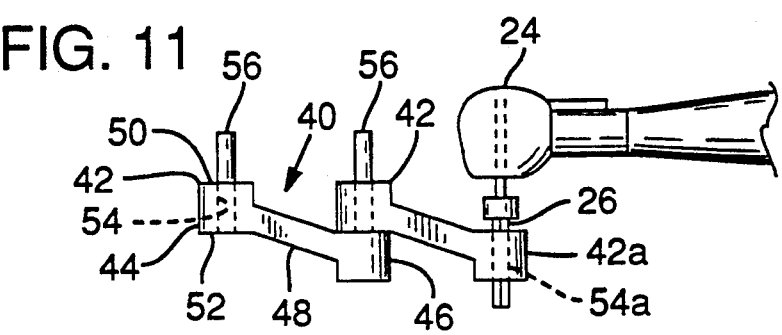
FIG. 11 is a side elevational view of a further embodiment wherein the end link of the articulated arm has a guide hole for a burr.
Figure 12:
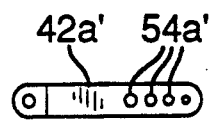
FIG. 12 is a plan view of the end link of FIG. 11 but modified to accommodate different sizes of burrs.
Figure 13:
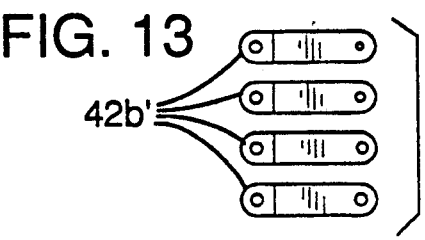
FIG. 13 is a plan view of a set of end links having guide holes of varying diameters to accommodate different size burrs.

Modified guiding connections can be made between the articulated arm 40 and the handpiece 24. In one embodiment, FIGS. 9 and 10, an adapter link 70 has end holes 72 and 74. The hole 72 is of a diameter to fit the post 56 of the arm 40 with close tolerance and the hole 74 is of a diameter to fit the shank 26 of the burr 26, also with close tolerance to maintain the flat, untwisting but pivotal relationship between the arm and the handpiece and also allowing up and down sliding movement on the post 56. In another embodiment, FIG. 11, the end link 42a of the arm 40 at its free end has its bore 54a of a selected diameter to receive the cutting portion of the burr 26 in a straight through guided relation. The bore 54a must accommodate a selected size of burr and for this purpose a set of the links 54a with appropriate sizes are provided, or, with reference to FIG. 12, the end link 42a'has bores 54a'of diameters that can accommodate the usual sizes of burrs. Also, as seen in FIG. 13, a set of end links 42b' can be provided each having a selected diameter of bore corresponding to the usual burr sizes.

It is to be understood that the forms of my invention herein shown and described are to be taken as preferred examples of the same and that various changes in the shape, size and arrangement of parts may be resorted to without departing from the spirit of my invention, or the scope of the subjoined claims.

Having thus described my invention, I claim:

1. A dentistry implant paralleling device comprising:
   an arm having forward and rearward ends,
   support means on the rearward end of said arm,
   base means capable of being associated with a person's mouth engageable by said support means,
   said base means comprising an anchor member having means for temporarily anchoring said base means in an implant hole cut in the jaw at a predetermined angle and capable of supporting said arm in cantilevered pivot arrangement in a person's mouth,
   and handpiece guide means on the forward end of said arm capable of guiding a burr for drilling a hole in the jaw at an angle parallel with said base means.

2. The implant paralleling device of claim 1 wherein said arm comprise an articulated member capable holes are to be drilled, said articulated arm being made up of at least two identical adjoining links, each of said links comprising a support surface that is maintained in a common plane with support surfaces of adjoining links and with said base means wherein said handpiece guide means is capable of guiding a burr parallel with said base means.

3. The implant paralleling device of claim 1 wherein said handpiece guide means comprises an upstanding post, and adapter link means having slidable and pivotal relation with said post and with a shank of a burr on the handpiece and maintaining a parallel relationship between the burr and said base means, said adapter link means having at least two different apertures for selected guiding of different sizes of burrs.

4. The implant paralleling device of claim 1 wherein said handpiece guide means comprises an end link on the forward end of said arm having a bore capable of receiving a cutting portion of a burr and guiding such cutting portion to maintain a parallel relationship between the burr and said base means.

5. A method of installing implants in a person's jaw comprising:
   establishing a first implant hole in the jaw that extends in a direction parallel with the intended angular direction of an implant to be installed in the jaw,
   installing a temporary anchor member in said opening,
   and using said anchor member as a pivot guide for arm means capable of projecting from said anchor member in cantilevered relation and guiding a handpiece for cutting implant holes in the jaw that are parallel with said first implant hole.

6. The method of claim 5 which uses an articulated member as said arm means for shaping said member at pivot portions thereof that extend parallel with said base.

7. A dentistry implant paralleling device comprising:
   an arm having forward and rearward ends,
   support means on the rearward end of said arm,
   an anchor member capable of being associated with a person's mouth engageable by said support means,
   said anchor member comprising a body portion for temporary installation in the jaw and having an end post pivotally supporting said arm in cantilevered pivot arrangement in person's mouth, and
   handpiece guide means on the forward end of said arm capable of guiding a burr for drilling a hole in the jaw at an angle parallel with said base means.

8. A dentistry implant paralleling device comprising:
   an articulated arm having forward and rearward ends,
   support means on the rearward end of said arm,
   base means capable of being associated wit a person's mouth engageable by said support means,
   said base means extending at a predetermined angle and capable of supporting said arm in cantilevered pivot arrangement in a person's mouth,
   and handpiece guide means on the forward end of said arm capable of guiding a burr for drilling a hole in the jaw at an angle parallel with said base means,
   said articulated arm being made up of at least two identical adjoining links, each of said links comprising a support surface that is maintained in a common plane with support surfaces of adjoining links and with said base means wherein said handpiece guide means on said articulated arm is capable of guiding a burr parallel with said base means and reach points on the jaw at which holes are to be drilled,
   said links being detachably connected together for using a selected number thereof and for varying the length of said arm.

9. The implant paralleling device of claim 8 wherein each of said links includes a pair of said support surfaces, said support surfaces being offset and including respectively guide post receiving means and a guide post.

10. The implant paralleling device of claim 8 wherein each of said links includes a pair of said support surfaces, said support surfaces being offset and including respectively guide post receiving means and a guide post, and cap means removably mounted on said post for maintaining adjoining links in connected but detachable relation.

* * * * *

UNITED STATES PATENT AND TRADEMARK OFFICE
CERTIFICATE OF CORRECTION

PATENT NO. : 5,302,122
DATED : April 12, 1994
INVENTOR(S) : ROBERT H. MILNE

It is certified that error appears in the above-identified patent and that said Letters Patent is hereby corrected as shown below:

In Column 5, line 2, after "capable" insert: -- of being laterally shaped to reach points on the jaw at which--

Signed and Sealed this

Sixteenth Day of August, 1994

*Attest:*

BRUCE LEHMAN

*Attesting Officer*     *Commissioner of Patents and Trademarks*